United States Patent
Worthington

(10) Patent No.: US 6,257,892 B1
(45) Date of Patent: *Jul. 10, 2001

(54) SHELLS FOR TEMPORARY AND PROVISIONAL CROWNS WITH AN HOURGLASS SHAPED OCCLUSAL PROFILE

(75) Inventor: Mark L. Worthington, Eugene, OR (US)

(73) Assignee: Flexible Dimensions, LLC, Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/484,944

(22) Filed: Jan. 18, 2000

Related U.S. Application Data

(63) Continuation-in-part of application No. 09/178,023, filed on Oct. 23, 1998, now Pat. No. 6,068,481.
(60) Provisional application No. 60/063,410, filed on Oct. 28, 1997.

(51) Int. Cl.$^7$ ........................................................ A61C 5/08
(52) U.S. Cl. ........................................... 433/219; 433/218
(58) Field of Search .................................... 433/219, 218, 433/40

(56) References Cited

U.S. PATENT DOCUMENTS

| | | | |
|---|---|---|---|
| 523,472 | * 7/1894 | Hollingsworth | 433/218 |
| 4,015,332 | * 4/1977 | Manne | 433/219 |
| 4,433,959 | * 2/1984 | Faunce | 433/222.1 |
| 4,678,435 | * 7/1987 | Long | 433/218 |
| 4,710,127 | * 12/1987 | Bellavia et al. | 433/218 |
| 4,778,386 | * 10/1988 | Spiry | 433/45 |
| 4,795,345 | * 1/1989 | Ai et al. | 433/202.1 |
| 5,454,716 | * 10/1995 | Banerjee et al. | 433/20 |
| 5,458,489 | 10/1995 | Tennyson | 433/181 |
| 5,679,710 | * 10/1997 | Davy et al. | 514/547 |
| 5,775,909 | * 7/1998 | Langer | 433/218 |
| 5,839,900 | * 11/1998 | Billet et al. | 433/218 |

* cited by examiner

Primary Examiner—John J. Wilson
(74) Attorney, Agent, or Firm—Marger Johnson & McCollom, P.C.

(57) ABSTRACT

A set of fiber-polycarbonate shells for making bicuspid and molar crowns are formed with hourglass shaped occlusal profiles. Mesio-distal sidewalls of the shells have a concave shape matching the concavity of the occlusal profile. The shells are sized to fit loosely between adjacent teeth and relative to opposed teeth. The concavity of the mesio-distal sides and the occlusal surface of each shell allows a good fit between the shell and the convex sides of adjacent teeth. A good fit provides a substantially uniform-width proximal gap between mesio-distal sidewalls of the shell and the adjacent teeth. Each shell further has small mesio-distal windows in the mesio-distal sidewalls. The uniform-width gap and the mesio-distal windows control mesio-distal resin flow to adjacent teeth. A new method of forming crowns using such shells provides a good fit to a prepared tooth and relative to adjacent and opposed teeth by filling the shell with a glass-filled acrylic resin filler and then positioning the shell gingivally and occlusally. Resin extrudes through the window to form good proximal contacts, with the shell rocking about the facial gingival margin to a comfortable fit with an opposed tooth. The excess resin and shell are shaped to form the final crown. The crown, formed by Ti particle reinforced resin, is durable enough for long-term wear.

35 Claims, 10 Drawing Sheets

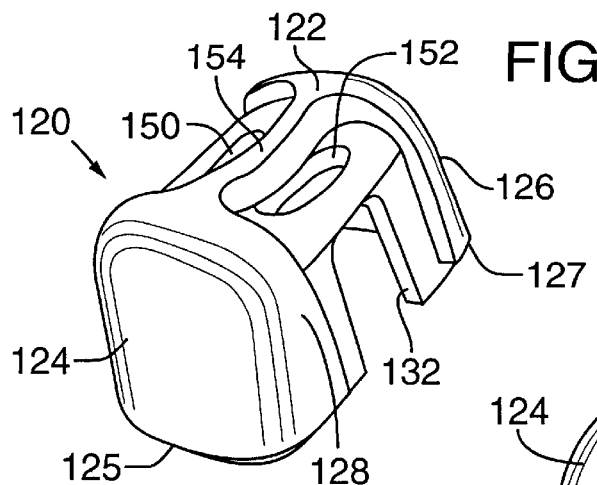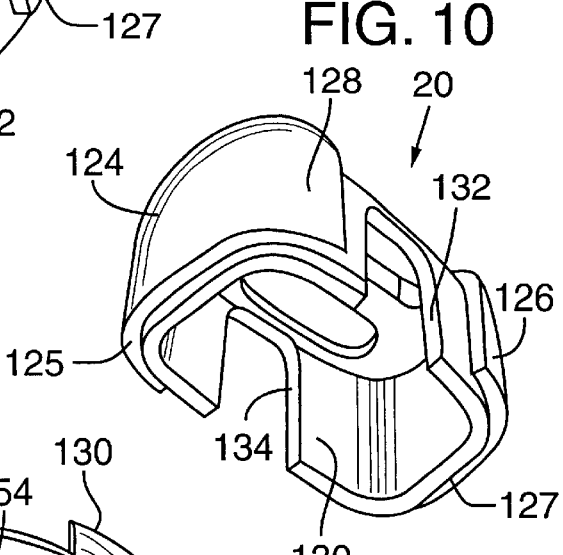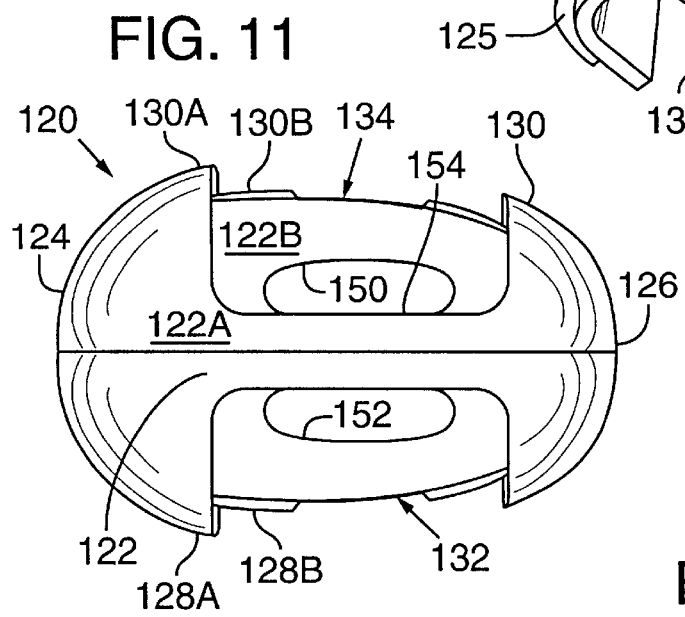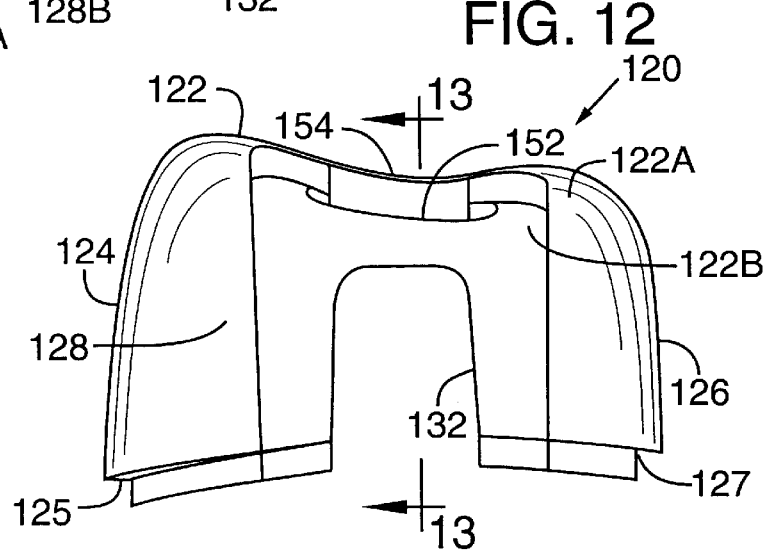

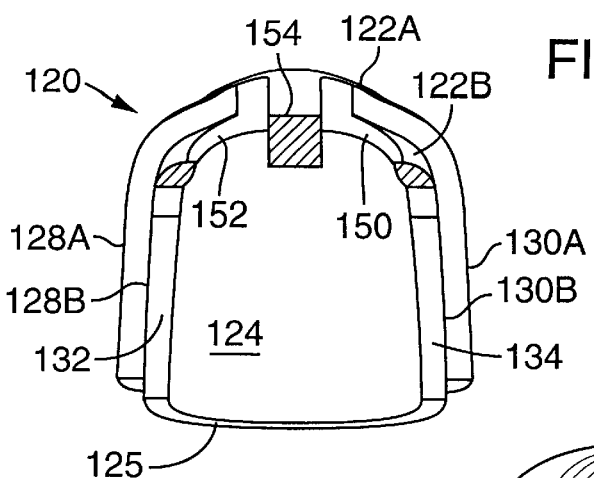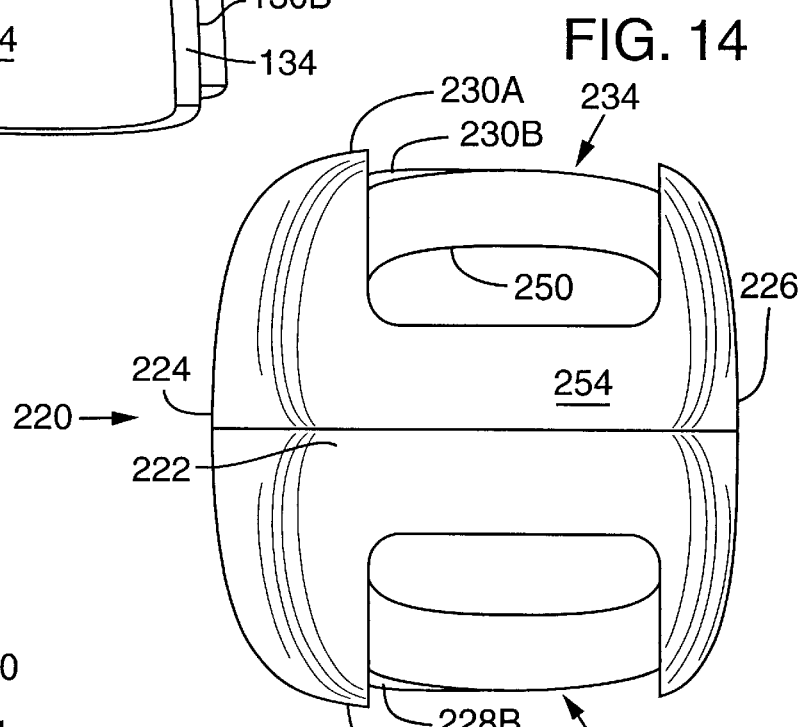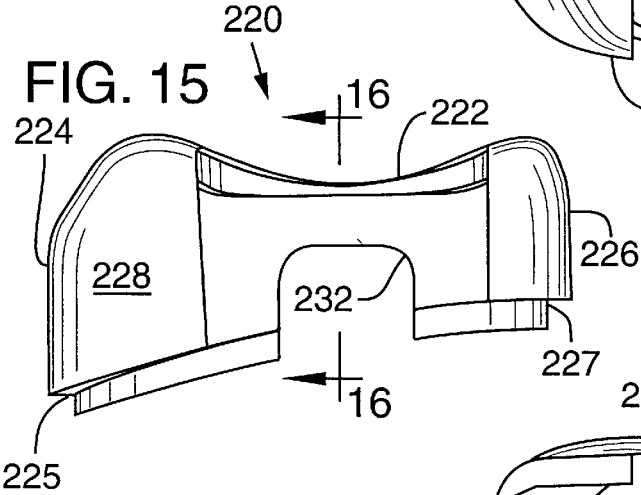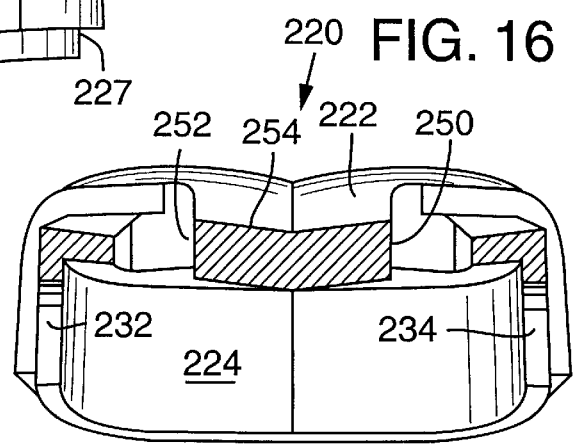

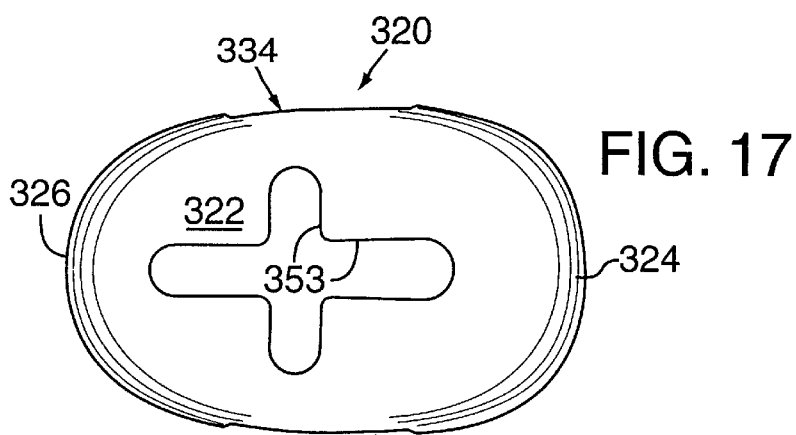
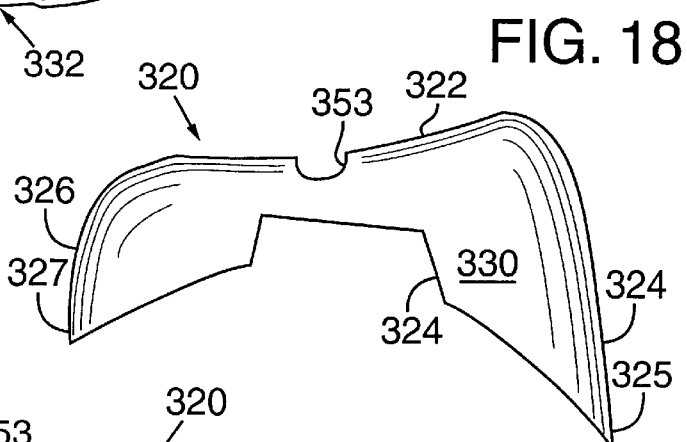
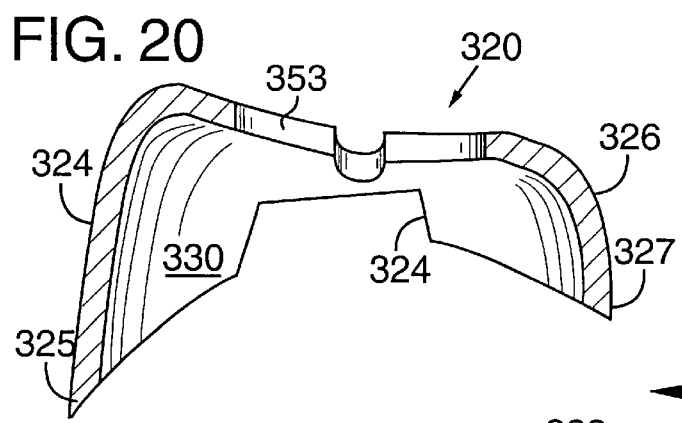
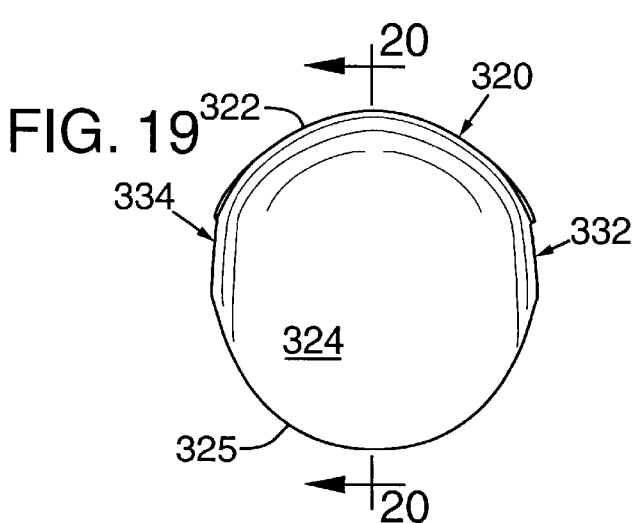

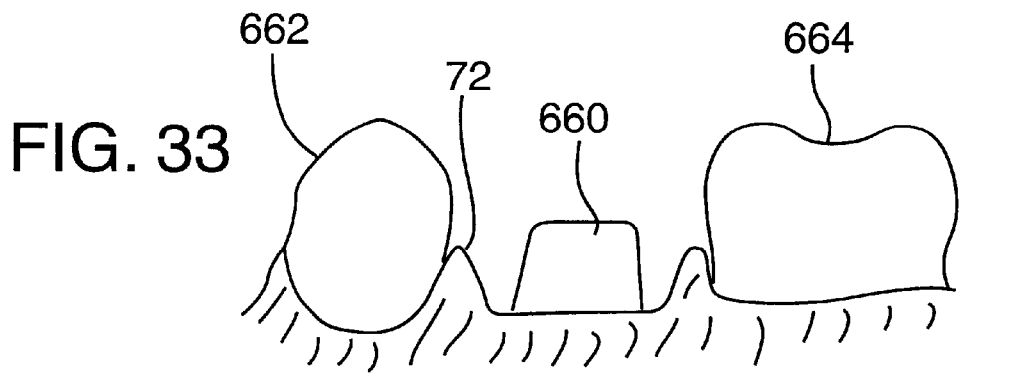
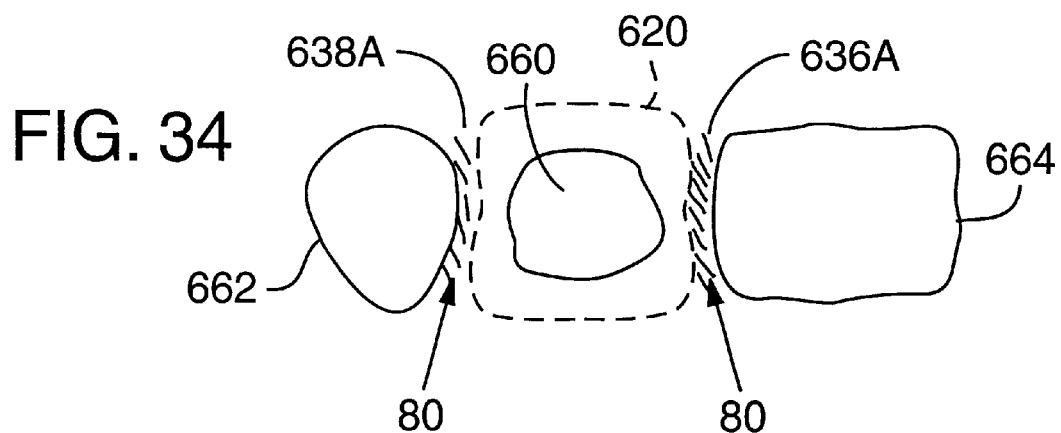
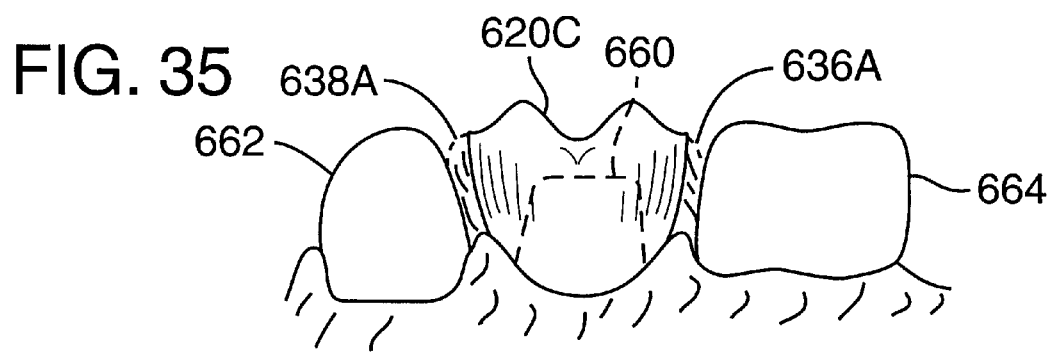

SHELLS FOR TEMPORARY AND PROVISIONAL CROWNS WITH AN HOURGLASS SHAPED OCCLUSAL PROFILE

This application is a continuation-in-part of U.S. Patent Application Ser. No. 09/178,023, filed Oct. 23, 1998, now U.S. Pat. No. 6,068,481, claiming priority from provisional U.S. Ser. No. 60/063,410, filed Oct. 28, 1997, and claims priority from provisional U.S. Ser. No. 60/131,817, filed Apr. 29, 1999, both incorporated herein by reference.

BACKGROUND OF THE INVENTION

This invention relates generally to temporary and provisional dental crowns, and more particularly to flexible dimension crown shells and methods of making temporary and long-term provisional dental crowns using such shells.

Presently, there are three primary methods for fabricating temporary and provisional crowns. In a first technique, conventional prefabricated crown forms or shells, made of a metal such as aluminum or stainless steel, or of a polycarbonate such as the Ion crown forms sold by 3M Corporation, are trimmed and shaped to fit a prepared tooth. Examples of temporary crowns of this type are disclosed in U.S. Pat. No. 4,015,332 (Manne), U.S. Pat. No. 4,678,435 (Long), U.S. Pat. No. 4,778,386 (Spiry), and U.S. Pat. No. 5,458,489 (Tennyson).

A second technique calls for making an impression of the tooth before the tooth is prepared for a crown. After the impression is made, the tooth is prepared and the impression, filled with a bis-acryl material, is placed over the prepared tooth. After the bis-acryl material sets, it is removed from the dental impression, and then trimmed, polished, and seated in the mouth.

A third primary technique, which is used and recommended by Gordon Christenson, is also popular. According to the third technique, a putty-like ball of polymethylmethacrylate is applied over a prepared tooth. The patient then bites down and the material begins to set. Before it completely sets, the putty-like material is removed from the tooth, trimmed and placed back on the tooth. Once the material sets, it is then trimmed again and the bite adjusted. Finally, the temporary crown is cemented to the tooth. In a variation of this technique, as disclosed in U.S. Pat. No. 5,385,469, a tubular dental form for forming a universal crown in situ is used.

Each of these techniques has various advantages and disadvantages. Using prefabricated forms, as in the first technique, for example, is fast and simple, but the fit of the conventional shell is not very good. The margins, in particular, do not fit well. Specifically, it is hard to get good proximal contact to adjacent teeth, and the contours and occlusion are not always good. Some manufacturers try to overcome these drawbacks by proliferating sizes and shapes of shells, with some selections providing as many as 80 different sizes and shapes of molars and bicuspids. Unfortunately, this attempted solution is expensive in terms of materials and also in terms of the time required for the dentist to pick the right shell.

Manne adds a degree of freedom to the first technique by providing an incisor shell that has slits in the mesio-distal sides to permit the shell to flex in the labio-lingual direction about a hinge axis at the occlusal surface. Long also provides a degree of freedom in this technique by having the mesio-distal sides of a temporary molar crown open to permit the acrylic resin filler material to protrude proximally to contact adjacent teeth. These shells, like others used in this technique, require trimming the free edges of their buccal and lingual sidewalls to ensure a good fit along the gingival margins, as well as a good occlusion. The shells in Long also appear to require substantial trimming of the filler material due to their open mesio-distal sides. Such trimming and fitting is time-consuming for the dentist and the patient.

The second technique gives good contours and bite accuracy, but making an impression is time-consuming. Furthermore, neither the strength nor the durability of temporary crowns produced by this technique are very good. Furthermore, the impression cannot be made if the patient's tooth is already broken when initially treated. The third technique, namely, free-forming a temporary crown of putty-like material, can be accurate and fairly fast compared to the other techniques, but only if performed by a skilled dentist or technician. It, too, however, is more time-consuming than desirable. Another main problem with this approach is that it is very technique-sensitive. A dental technician must be highly skilled in order to accurately carve the tooth anatomy. Another problem with this technique is that special care must be taken to ensure that the patient's mouth is not injured by the exothermal reaction involved in curing the crown material.

As noted, all of the foregoing techniques are undesirably slow. Even the fastest of these techniques generally takes half an hour or more of work for the dentist to fit a temporary or provisional crown to a patient. Additionally, the crowns resulting from the second and third techniques are typically not very durable and are therefore not well-suited for long-term wear. Although the stainless steel shells of the first technique are very durable, it is more difficult to fit stainless steel shells to the patient and to grind the shells' occlusal surfaces to get a comfortable bite.

Accordingly, a need remains in the profession for a way of making temporary and provisional crowns that is quick and accurate, that provides a good fit without substantial trimming, that is durable enough for long-term use, and that is inexpensive.

SUMMARY OF THE INVENTION

It is, therefore, an object of the invention to simplify the fabrication, fitting, and installation of temporary and provisional crowns.

Another object of the invention is to make temporary and provisional crowns that fit well and are durable enough for long-term use.

A further object is to make crowns that fit well but are inexpensive both in terms of materials and time taken to fit the crowns.

In general, the invention combines two of the conventional techniques, namely, the free-form and specially-designed shell techniques, in a way that takes the advantages of, yet avoids the major disadvantages of, both of these techniques as used individually. Specifically, the shells of the invention have a generally U-shaped window, unbounded along a gingival margin, in at least one of the mesio-distal sidewalls. A putty-like material or resin is used, similar to that used in the free-form technique, but in this case it is shape-controlled by the shell and the windows provided therein. This shape control saves the dentist valuable time in shaping the temporary or long-term provisional crown. The mesio-distal sidewalls each include a recessed area or indentation adjoining the windows for receiving and retaining protruding resin in proximal contact with adjacent teeth. The shells are further designed with short labial and lingual side walls so that no trimming of the shells themselves is needed. This, too, saves the dentist a great deal of time. The shells also give the dentist several degrees of freedom, so that most molars and bicuspids can be fitted with only a limited range of sizes and shapes of symmetric shells.

A particular shell for making a temporary or long-term provisional crown on a prepared tooth includes a top wall, a buccal sidewall; a lingual sidewall, and opposite mesio-distal sidewalls. The top wall defines an occlusal surface of the shell. The mesio-distal sidewalls are each connected to the top wall and to the buccal and lingual sidewalls, and are spaced apart from each other to define a central cavity. The central cavity is configured to receive resin and to fit over a prepared tooth. A window is formed in at least one mesio-distal sidewall to provide a partial opening that allows a portion of the resin to protrude mesio-distally from the cavity to an adjacent tooth. Furthermore, at least one of the mesio-distal sidewalls is shaped concavely to interfit with a convex mesio-distal surface of the adjacent tooth.

Preferably, the top wall of the shell is shaped concavely along mesio-distal edges to form an approximate hourglass shape conforming to a convex shape of mesio-distal surfaces of adjacent teeth, with both of the mesio-distal sidewalls shaped to align with the concavity of the top wall. In this way, the concave mesio-distal sidewall can provide an approximately uniform-width gap between the shell and the convex adjacent tooth and control a proximal flow of the resin.

A method of fabricating temporary or long-term provisional crowns for molars and bicuspids is also provided. The method includes filling a central cavity of a shell with a quantity of resin. The shell has a top wall defining an occlusal surface, opposite buccal and lingual sidewalls, and opposite mesio-distal sidewalls spaced apart to define the central cavity. The resin-filled shell is positioned on a prepared tooth and a portion of the resin is extruded mesio-distally through a window forming a partial opening in at least one of the mesio-distal sidewalls. While the resin sets, the shell and resin are repeatedly put on and pulled off of the prepared tooth until the resin is set. After the resin has completely set, the shell and extruded resin are shaped to contour an external surface thereof to fit occlusally and proximally into the patient'mouth.

Extrusion of the resin is controlled by sizing the windows to encompass only a limited portion of the mesio-distal side area. Further control is provided by the concavity of the mesio-distal sidewall relative to the convexity of the adjacent tooth. This arrangement provides a uniform mesio-distal gap to receive and retain the resin.

Shaping the crown preferably proceeds by marking the mesial and distal contacts and margins of the crown after it has been removed from the prepared tooth. Resin that has extruded through the window in the mesio-distal sidewall is removed beyond the marked contacts and margins. Following shaping, the shell and resin are repositioned on the prepared tooth.

Further advantages can be obtained by this invention if the resin contains Ti particles to improve the strength and durability of the crown. Also, the shell and resin can be made to contain radio-opaque substances, so they will appear on x-rays.

Long-term provisional crowns made according to this invention provide an alternative to high cost crowns, offering benefits to patients, dentists, and insurance companies. Both temporary and long-term provisional crowns made according to this invention are accurate, can be made very fast, and are more durable than most of the prior art. Crowns made using the long-term provisional shells should last 5–7 years or longer. Crowns made using the temporary shells (having slightly thinner walls than in provisional shells) last from 3–4 months up to about 1 year. Crowns made according to this invention are also simpler and easier to install than molded crowns and are much more accurate than pre-fab crowns. The crowns of this invention offer good margins, good contacts, and good occlusions to prevent tooth shift while waiting for permanent crown. They are also more comfortable for the patient and are aesthetically attractive.

The present invention enables temporary or provisional crowns to be fitted to a patient quickly, i.e., in half the time (or less) required by prior art techniques; to provide a good fit proximally, gingivally, and occlusally; and to provide long-term durability.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIGS. 9 and 10 are top and bottom perspective views, respectively, of a bicuspid shell according to a second embodiment of the invention.

FIGS. 11 and 12 are plan and mesio-distal side elevation views, respectively, of the shell of FIGS. 9 and 10.

FIG. 13 is a cross-sectional view taken along line 13—13 in FIG. 12.

FIGS. 14–16 are plan, side elevation, and cross-sectional views, similar to FIGS. 11–13, respectively, showing a shell for a molar according to the invention.

FIGS. 17–20 are plan, side elevation, buccal end, and cross-sectional views, respectively, of a shell for a bicuspid according to a third embodiment of the invention.

FIGS. 33–35 are a side elevation view, a plan view, and another side elevation view, respectively, illustrating how a shell for a molar according to the fourth embodiment of the invention is placed on a prepared tooth.

DETAILED DESCRIPTION

FIGS. 1–5 illustrate the basic concept of the present invention in a first embodiment with respect to a bicuspid crown. Although these figures are specifically directed toward bicuspid crowns, the following description applies equally to crowns for molars. Molar crowns are more specifically described in connection with subsequent figures.

Figure 1:
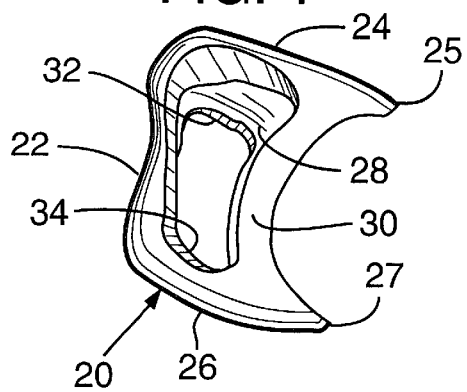
FIG. 1 is a side elevation view of a polycarbonate shell for making a temporary crown according to a first embodiment of the invention.

FIG. 1 is a side elevation view of a shell 20 for making a temporary or long-term provisional bicuspid crown. The shell 20 is preferably integrally molded of polycarbonate material but can be made of other polymeric materials and can be machined rather than molded. The shell 20 has a top wall 22 that defines an occlusal surface; a buccal sidewall 24; and a lingual sidewall 26 spaced from the buccal sidewall. The buccal sidewall 24 can include a detachable tab (not shown) for handling the shell during making of the crown. Opposite mesio-distal sidewalls 28, 30, are connected to the top wall 22 and the buccal and lingual sidewalls 24, 26, and are spaced apart from each other to define a central cavity. The central cavity is shaped to receive an acrylic resin and to fit over a prepared tooth.

The lingual sidewall 26 is shorter than the buccal sidewall 24 for ease of fitting the gingival margins 25, 27, as further discussed below. The mesio-distal sidewalls 28, 30 are shorter occluso-gingivally than the buccal and lingual sidewalls 24, 26. Shells of various sizes can be provided, including shells having two or more different occluso-gingival lengths of the lingual and buccal sidewalls, to better serve a wide range of tooth lengths.

Each of the mesio-distal sidewalls 28, 30 includes a mesio-distal window 32, 34 that forms a partial opening in its respective sidewall. The mesio-distal windows 32, 34 allow the acrylic resin to protrude proximally from the cavity to adjacent teeth when the resin-filled shell 20 is fitted on a prepared tooth 60 (see FIG. 6). Although the shell 20 can be made and used with a mesio-distal window in only one sidewall, it preferably has windows in both mesio-distal sidewalls 28, 30. Each mesio-distal window 32, 34 is sized to allow resin to protrude therefrom in an amount sufficient to form a good proximal contact 36A, 38A (see FIG. 2) with an adjacent tooth; but is sized sufficiently smaller than an overall size of the mesio-distal sidewall 28, 30 in order to control the flow of resin from the central cavity. The mesio-distal windows 32, 34, for example, have an area of about half the overall area of the mesio-distal sidewall of the shell.

The preferred material for making the shells 20 of the invention is a 20% fine fiber-glass filled polycarbonate. The material forming shell 20 may also include a radio-opaque substance, such as barium sulfate (BaS), so that it will show up on x-rays. The resin used in the invention is preferably Super-T glass-filled acrylic resin and also preferably contains BaS or some other radio-opaque substance so that it will also appear on x-rays. Furthermore, fine size titanium (Ti) particles or powder can be added to the resin to make the resulting crown more durable and thereby increase its longevity.

Figure 2:
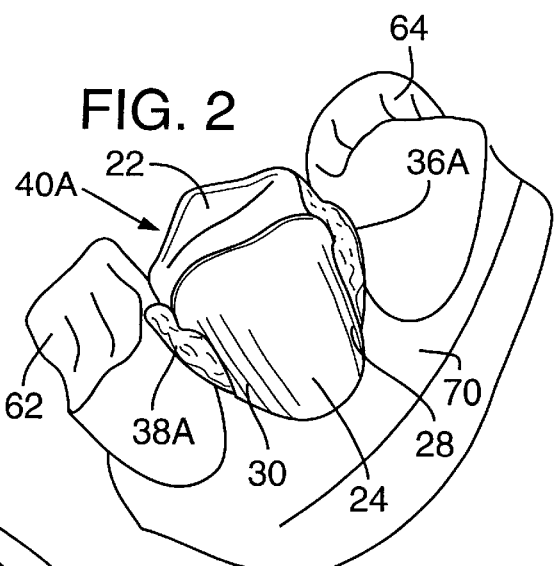
FIG. 2 is a perspective view of a temporary crown made by filling the shell of FIG. 1 with acrylic resin, which extrudes through windows in the mesio-distal sides of the temporary crown, and placing the shell over a prepared tooth.

FIGS. 2–5 illustrate a method for fabricating a temporary or long-term provisional bicuspid crown using the shell 20 shown in FIG. 1. FIG. 2 is a perspective view of a portion of a patient's mouth showing a temporary or long-term provisional bicuspid crown 40A. Referring to FIGS. 1 and 2, a temporary or long-term provisional crown 40A is made by filling the central cavity of the polycarbonate shell 20 with a quantity of Super-T acrylic resin and by positioning the resin-filled shell on the prepared tooth. The patient then bites down, clamping the resin-filled shell 40A against an opposing tooth 66 (see FIG. 8) and thereby establishing an occlusal contact of the occlusal surface 22 of the shell 20 with the opposing tooth 66. This step also shapes the resin within the cavity to mate with the prepared tooth 60 (see FIG. 8).

Furthermore, when the patient bites down on the shell 20, a portion of the resin is extruded from the cavity through the mesio-distal windows 32, 34. A portion of the mesio-distal sidewalls 28, 30 along the buccal and lingual margins of each mesio-distal window 32, 34 directs the extrusion of resin proximally toward the adjacent teeth 62, 64. The resin extruded through these windows thereby forms mesio-distal protrusions 36A, 38A that contact adjacent teeth on proximal sides of the temporary crown.

The shells 20 are also preferably formed with the lingual sidewall 26 slightly shorter than the buccal sidewall 24. This sizing permits a degree of freedom in positioning the occlusal or top wall 22, as the patient bites down, without the gingival margin 27 of the lingual sidewall 26 engaging the patient's gingival 70. This feature is explained in further detail below.

Figure 3:
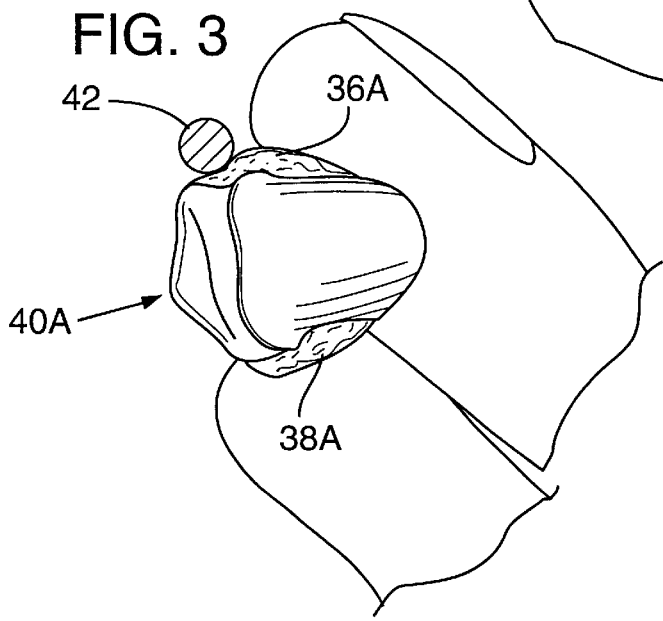
FIG. 3 is a perspective view of the temporary crown of FIG. 2 having been removed from the patient's tooth for shaping of the extruded resin using an acrylic burr.

FIG. 3 shows the temporary crown 40A of FIG. 2 removed from the patient's tooth and held in a dentist's fingers. Referring now to FIG. 3, the protrusions 36A, 38A of the temporary crown 40A are trimmed and shaped using an acrylic burr 42 to contour the crown's external surface to fit into the patient's dentition both occlusally and proximally. Trimming the gingival margins of shell 20 is generally unnecessary.

Figure 4:
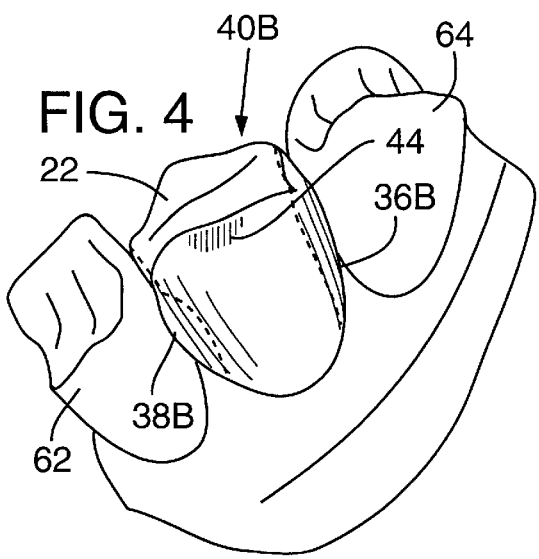
FIG. 4 is a perspective view similar to FIG. 2 showing the shaped temporary crown replaced on the patient's prepared tooth, with shading along the edge of the occlusal surface indicating an area to be ground for bite adjustment.
Figure 5:
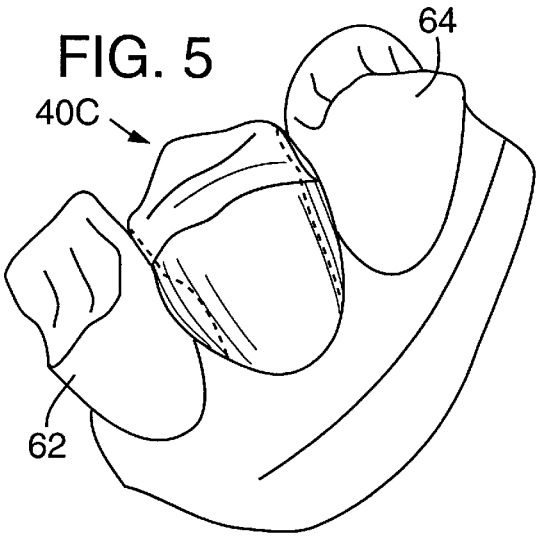
FIG. 5 is a perspective view similar to FIG. 4 showing the temporary crown after shaping for bite adjustment, with broken lines indicating the portion of the temporary crown formed by the extruded and shaped resin, which protrudes through the windows on the mesio and distal sides of the crown.

FIG. 4 shows the temporary crown 40B, with shaped extrusions 36B, 38B, placed back on the patient's prepared tooth. Shading 44 along an edge of the occlusal surface 22 indicates a buccal cusp of the temporary crown to be ground for bite adjustment. FIG. 5 shows the temporary crown 40C after shaping for bite adjustment. The dashed lines in FIGS. 4 and 5 indicate the portion of the temporary crown formed by the extruded and shaped resin, which protrudes through the windows on the mesio-distal sides of the crown 40C. The resulting crown is composed of polycarbonate- reinforced acrylic resin which is very durable. The crown is therefore suitable for use as a long-term provisional crown as well as a temporary crown.

Once the crown is finished, the border between the shell and filler material is substantially smooth and nearly invisible except upon close inspection. The finished crown 40C is cemented and tightly sealed to the patient's prepared tooth 60 (see FIG. 8) along the gingival margins 25, 27 to secure it within the patient's dentition. The resulting proximal fit to adjacent teeth 62, 64 closely replicates that of a natural tooth, as does the occlusion with opposed teeth 66 (see FIG. 8).

According to this invention, the entire procedure for providing a temporary or long-term provisional crown, i.e., from picking the properly sized shell through filling, shaping, and cementing the crown onto the prepared tooth, takes about half the time required by the prior art. Remarkably, the entire procedure can typically be completed in under 15 minutes.

Figure 6:
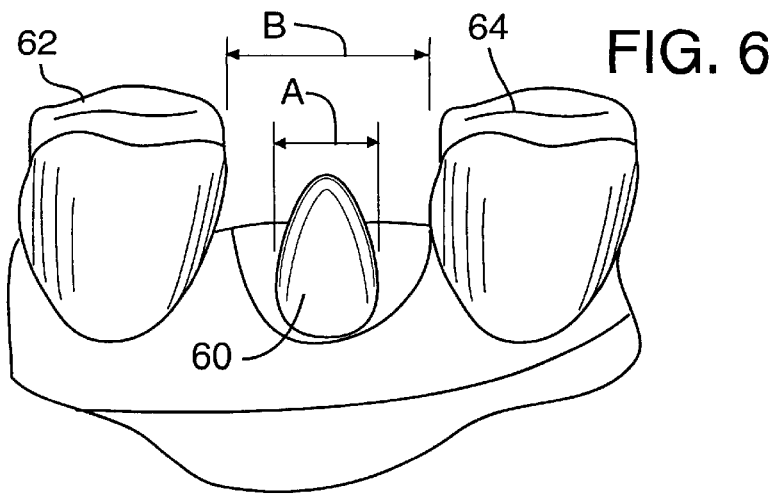
FIGS. 6 and 7 are side and plan views, respectively, of a portion of a patient's dentition showing spacings used to select a shell of proper mesio-distal size to fit a prepared tooth according to the invention.
Figure 7:
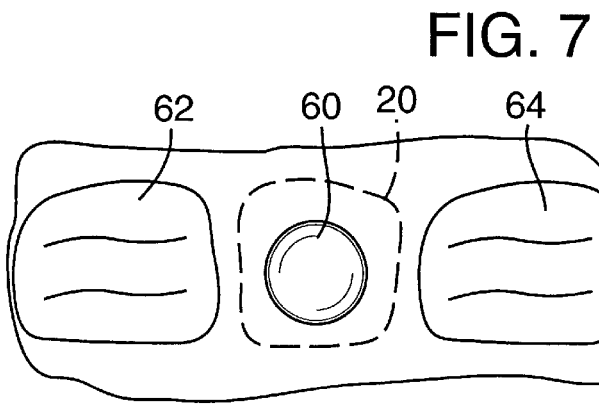
Figure 8:
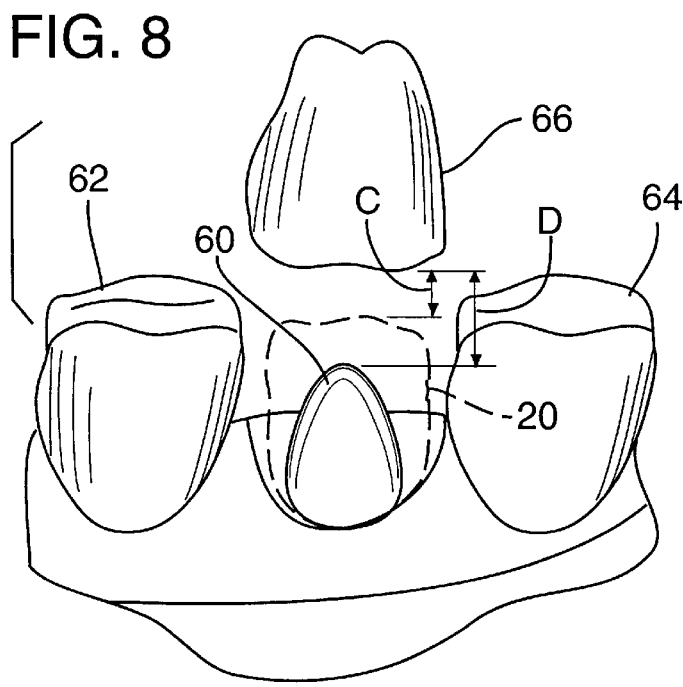
FIG. 8 is a side view similar to FIG. 6 showing sizing dimensions in the occluso-gingival direction.
Figure 21:
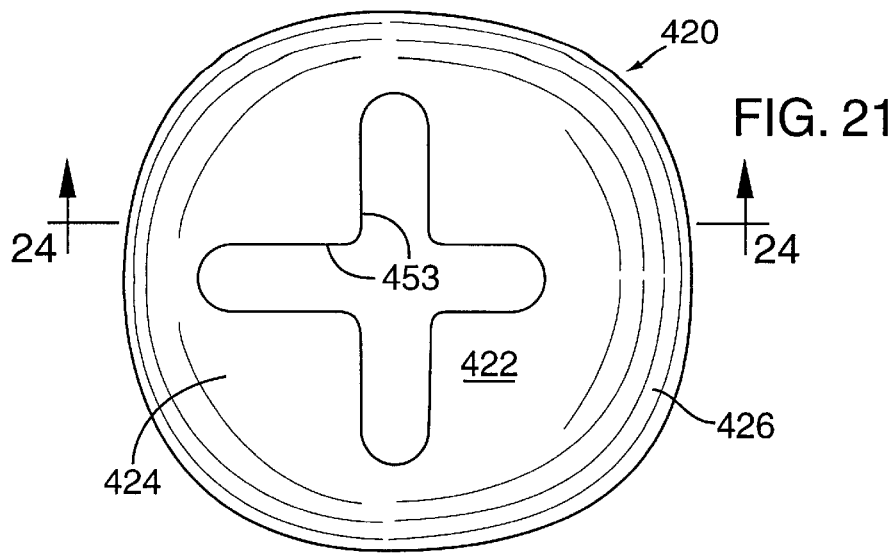
FIGS. 21–24 are plan, side elevation, buccal end, and cross-sectional views, similar to FIGS. 17–20, respectively, of a shell for a molar according to the third embodiment of the invention.
Figure 22:
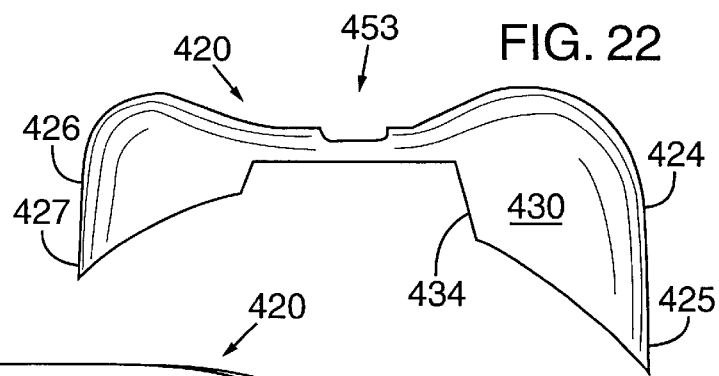
Figure 23:
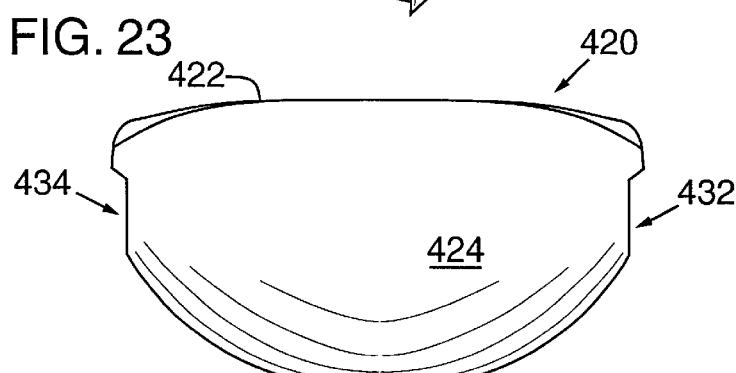
Figure 24:
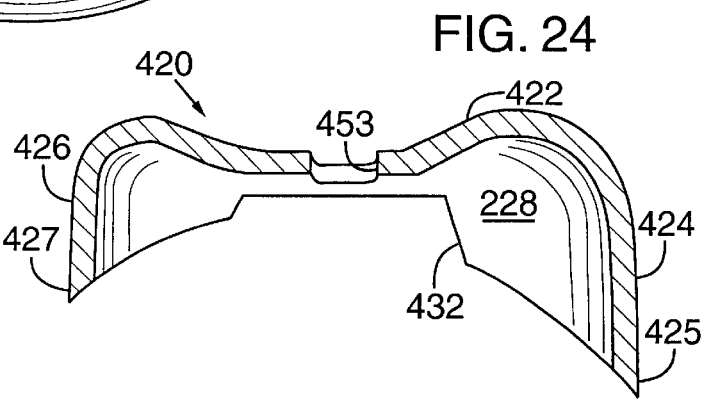

FIGS. 6–8 show various views of a portion of a patient's dentition to illustrate an example of spacings used to select a shell of a proper mesio-distal and occluso-gingival size. A properly sized shell should fit loosely between adjacent teeth 62,64 on a prepared tooth 60 with the patient's bite in a closed position. FIGS. 6 and 8 show sizing parameters of the shell 20. FIG. 6 illustrates mesio-distal sizing parameters A, B for positioning the shell. Mesio-distal sidewalls of the shell are positioned approximately halfway between mesio-distal surfaces of the adjacent teeth 62, 64 and mesio-distal surfaces of the prepared tooth 60. In other words, the shell is centered between the prepared tooth's adjacent teeth with a width midway between width A and width B. The resulting position of shell 20 is shown by dashed lines in FIGS. 7 and 8. Using the embodiments of shells shown in FIGS. 9–16 or FIGS. 25–32, having recessed or concave mesio-distal sides, the proximal spacing is preferably closer, as described below with reference to FIGS. 33–35.

It is preferable to provide a set of shells that includes shells for bicuspids and molars of at least two mesio-distal widths within the usual range of spacings for such teeth in permanent dentition. These sizing options enable the dentist to select a shell for a given prepared tooth which has a mesio-distal width such that the shell passively fits between the adjacent teeth with a clearance in the range of one-half to one millimeter. The remaining proximal gap is filled by the mesio-distal resin protrusions 36A, 38A. This arrangement makes proximally fitting the crown very easy compared to prior art shells.

Referring to FIG. 8, the shell 20 is also sized having a length in an occluso-gingival direction that allows it to fit passively against an opposed tooth 66 when the patient's bite is in a closed position over the unfilled shell 20. Similar to above, a set of shells can include two different occluso-gingival lengths of a given bicuspid or molar, to accommodate the usual range of variations in tooth length that occurs among humans. For a given prepared tooth length, the shell is sized occluso-gingivally to provide a clearance C that is approximately half of the width D of the space between the occlusal wall of the shell 20 and the opposed tooth 66. The shell 20, selected for a particular tooth, preferably has an occluso-gingival length such that a gingival margin of the shell approximately fits a gingival margin of the prepared tooth and such that the occlusal surface of the shell has a clearance from the opposed tooth 66 of one-half to one millimeter.

FIGS. 9–13 show various views of a second embodiment of a bicuspid shell 120 according to the invention. The general arrangement, materials, and procedure for making temporary and provisional crowns using shell 120 can be the same as those described above for shell 20 (see FIG. 1). The preferred sizing and method of fitting are described below with reference to FIGS. 33–44. The parts of shell 120 that correspond to parts in shell 20 are denoted by the same reference numerals, incremented by 100. Accordingly, shell 120 has an occlusal (or top) wall 122, buccal and lingual sidewalls 124, 126 with gingival margins 125,127, respectively, and proximal (mesio-distal) sidewalls 128,130.

Unlike the mesio-distal windows 32, 34 of the shell 20 of the first embodiment, however, which are bounded along the gingival margins of the mesio-distal sidewalls, the mesio-distal windows 132,134 of the shell 120 in this embodiment have a generally U-shape and unbounded along the gingival margins of the proximal sidewalls 132,134. The mesio-distal windows 132, 134 of this embodiment are also narrower than mesio-distal windows 32, 34 of the first embodiment, and preferably occupy an area that is about one-third of the overall area of the sidewall in which the window is formed.

Also unlike the first embodiment, at least one occlusal window can be provided in the occlusal wall 122. The occlusal wall 122 preferably includes a pair of occlusal windows 150,152, in the form of elongate ovals spaced about a central bridge 154. The occlusal windows 150,152 are configured to allow a controlled portion of resin from the central cavity of the filled shell 120 to be extruded onto the upper side of the occlusal wall 122 when the patient bites down on the shell 120 during the fabrication step described previously with reference to FIG. 2.

Referring specifically to FIG. 11, the top wall 122 of the shell 120 further includes a first occlusal surface 122A formed along the top of the central bridge 154 and on buccal and lingual sides of the top wall 122. A second occlusal surface 122B is also part of the top wall 122 but is formed recessed from the first surface 122A, surrounding mesio-distal, buccal, and lingual sides of the occlusal windows 150, 152. The second occlusal surface 122B thereby forms a recessed margin around the occlusal windows 150, 152 for receiving the resin extruded through those windows 150, 152 and for retaining the resin around them so that the resin can be shaped by contact with the occlusal surface of an opposed tooth 66 (see FIG. 8).

Similarly, the proximal surfaces 128, 130 of the shell 120 preferably include recessed surface areas 128B, 130B between the vertical sides of the windows 132, 134 and the shell's outermost proximal surfaces 128A, 130A. The recessed areas 128B, 130B form a recessed margin around the mesio-distal windows 132, 134 for receiving the resin extruded through those windows 132, 134 and for retaining the resin in proximal contact with adjacent teeth 62, 64 (see FIG. 8). This recessed or indented area provides a concavity that permits a closer fit to the convex proximal faces of adjacent teeth.

As best seen in FIG. 12, the gingival margins 125, 127 of the shell 120 of this embodiment can be formed with a stair-shaped cross-sectional profile. This profile, which can also be tapered, aids in receiving and retaining resin around the gingival margins 125, 127 to form a superior seal with the prepared tooth 60 (see FIG. 8). Another unique feature of this embodiment is that the lingual sidewall 126 is shorter than the buccal sidewall 124 by a ratio of about 3:4.

FIGS. 14–16 show a shell 220 for a molar having essentially the same design as the second bicuspid embodiment described above with reference to FIGS. 9–13. The structural elements and features of this embodiment that correspond to those shown in the previous embodiments are indicated by the same reference numerals, incremented by 200, and need not be further described. General differences in the size and shape of the bicuspid and molar shells 120, 220, respectively, are due to their respective applications in bicuspid and molar crowns. In addition to their general size and shape differences, another main difference between the molar shell 220 and the bicuspid shell 120 is that the molar lingual sidewall 226 is shorter than the molar buccal sidewall 224 by an even greater proportion than in the bicuspid shell 120. Specifically, the molar lingual sidewall 226 is shorter than the molar buccal sidewall 224 by a ratio of about 2:3, as compared to the 3:4 lingual-buccal sidewall ratio of the bicuspid shell 120.

FIGS. 17–24 show a bicuspid shell 320 and a molar shell 420 according to a third embodiment of the invention. Structural elements and features in common with the previously-described embodiments are indicated by like reference numerals incremented by 300 and 400 for the bicuspid and molar shells, respectively. The proximal sidewalls can also be recessed or indented (not shown) as shown and described with reference to FIGS. 9–16 and FIGS. 25–32.

There are several differences between the bicuspid and molar shells 320, 420 of this embodiment and the shells of the previous embodiments. First, the occlusal walls 322, 422 each have a single cross-shaped occlusal window 353, 453, best seen in FIGS. 17 and 21. This window arrangement provides somewhat more window area for resin extrusion onto the top walls 322, 422 as compared to the occlusal windows 150, 152 of the second embodiment, but still provides support for the filler in the finished crown. Second, the gingival margins of the shells are internally tapered, as shown by margins 325, 327 and 425, 427 in FIGS. 20 and 24, respectively. A third difference is that the lingual sidewalls 326, 426 are shorter than the buccal sidewalls 324, 424 by a still greater proportion than either of the previous embodiments, this time having a lingual-buccal ratio of about 1:2. This ratio gives the greatest freedom for positioning the gingival margin of the lingual sidewall vertically along the lingual side of the prepared tooth. This freedom of positioning allows the buccal cusp of the shell to be moved buccal-lingually about a gingival margin of the buccal sidewall. Although an even shorter lingual sidewall could be used, it is not desirable because it would not provide much more freedom for positioning the lingual margin or the buccal cusp and because it would result in less control of lingual resin flow along the gingival margin.

A further feature and advantage of the invention is best seen in the third embodiment. Specifically, this embodiment incorporates a generic design suited to fit all four quadrants of a patient's dentition easily. A kit consisting of four separately-sized molar shells and four separately-sized bicuspid shells (eight total), is provided. When sized as shown in FIGS. 7 and 8, this kit suffices to fit 95% of all permanent posterior dentition without trimming. Furthermore, the kit of this embodiment does not require right or left mirror-image shells for right or left dentition, nor does it require maxilla- and mandibular-specific shells.

This advantage is obtained because the shells 320, 420 are symmetrical about a buccal-lingual axis. Additionally, all of the sidewalls of the shells 320, 420 are short enough to fit a patient's dentition passively (i.e., without interference with the prepared tooth, adjacent teeth, or opposed teeth) when the patient's bite is in the closed position. The acrylic resin extrudes out of the mesio-distal sidewalls in a controlled way to form good proximal contacts with adjacent teeth. The resin also extrudes along the gingival margins of the shell to form an accurate marginal seal on all sides of the prepared tooth. Because the lingual sidewalls 326, 426 are substantially shorter than the buccal sidewalls 324, 424, the shells 320, 420 are free to rotate about the facial gingival margins 325, 425 of the buccal sidewalls as the patient bites down on the resin-filled shell. Accordingly, this arrangement eliminates the need to trim the shell margins, facilitates proper positioning of the buccal cusp of the shell relative to opposed teeth, and reduces the need to trim excess resin and shell material from the facial (buccal) and occlusal surfaces of the crown.

FIGS. 25–32 show a bicuspid shell 520 and a molar shell 620 according to a fourth embodiment of the invention. Structural elements and features in common with the previously-described embodiments are indicated by like reference numerals incremented by 500 for the bicuspid shell and 600 for the molar shell, respectively. There are several differences between this and the previous embodiments. First, the top wall 522, 622 does not have a window, as in the second and third embodiments, but is instead provided with a occlusal surface 522A, 622A that approximates the biting surface of a normal tooth, as in the first embodiment. Further, when viewed from the top, the occlusal wall 522, 622 has an approximate hourglass shape. This hourglass shape provides a profile that is roughly concave along the mesio-distal sides to allow the shell to conform to the convex shape of the mesio-distal sides of adjacent teeth. As in the second embodiment, the concave shape and spacing of the mesio-distal sides 528, 530, 628, 630 allows the shell to fit with an approximately uniform-width proximal gap 80 relative to the adjacent teeth (see FIG. 34).

The buccal sidewalls 524, 624 and lingual sidewalls 526, 626 are substantially triangular in shape (see FIGS. 27 and 31), and wrap around to form part of the mesio-distal sidewalls 528, 530, 628, 630. The buccal and lingual sidewalls 524, 526, 624, 626 can also be of equal or near-equal length, although the lingual sidewall is preferably slightly shorter than the buccal sidewall. These features (the triangular shape and nearly equal length of the buccal and lingual sidewalls) allow the shell to cover the inter-dental papilla 72 adjacent to the prepared tooth, as will be described with reference to FIGS. 33–34. As in the third embodiment of the invention, the gingival margins 525, 527, 625, 627 can be internally tapered.

The mesio-distal or proximal sidewalls 528, 530, 628, 630 are primarily formed as wrap-around portions of the buccal and lingual sidewalls 524, 526, 624, 626 and from downwardly wrapping edges of the occlusal wall 522, 622. The proximal sidewalls are shorter than the lingual sidewall. A portion of the mesio-distal sidewalls 528, 530, 628, 630 are open to provide mesio-distal windows 532, 534, 632, 634 through which resin can extrude into proximal gap 80. These mesio-distal windows 532, 534, 632, 634 are substantially smaller in size than those of the previous embodiments, and generally comprise less than ¼, and preferably between ⅛ to ¹⁄₁₀, of the surface area of their respective mesio-distal sidewalls. Although the mesio-distal windows 532, 534, 632, 634 are shown substantially trapezoidal in FIGS. 26 and 30, they can be provided with a substantially semicircular shape or simply be provided with rounded corners.

The mesio-distal sidewalls 528, 530, 628, 630 generally follow the concave shape of the mesio-distal sides of the occlusal wall 522, 622 in order to achieve the desired conformity with the adjacent teeth 62, 64. Most preferably, the shells 520, 620 are shaped and positioned to have a relatively uniform-width proximal gap 80 between the concave mesio-distal sidewalls 532, 534, 632, 634 and the convex mesio-distal sides of the adjacent teeth 62, 64, as shown in FIG. 34. A significant benefit of this aspect of the invention is that the concavity of the mesio-distal sidewalls of the shells fits the convexity of adjacent teeth.

Figure 25:
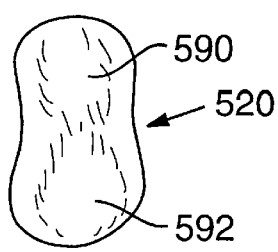
FIGS. 25–28 are plan, mesio-distal side elevation, buccal-lingual side elevation, and bottom views, respectively, of a shell for a bicuspid according to a fourth embodiment of the invention.
Figure 26:
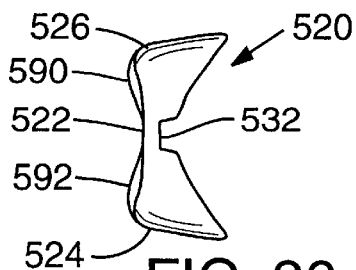
Figure 27:
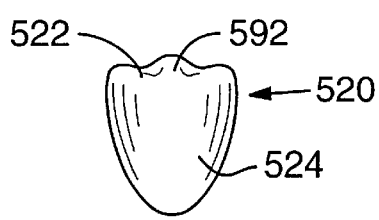
Figure 28:
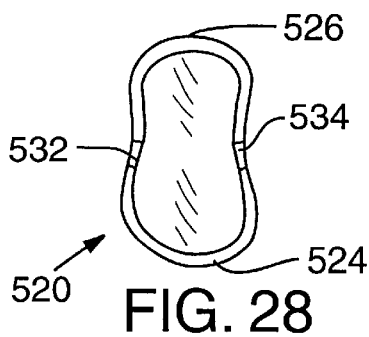
Figure 29:
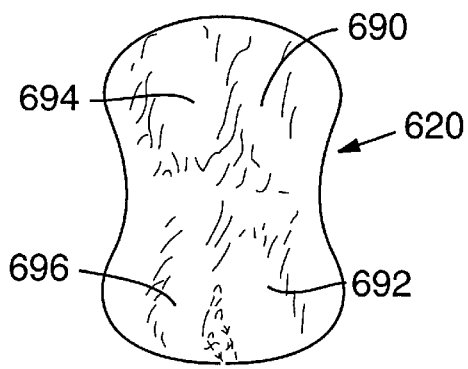
FIGS. 29–32 are plan, mesio-distal side elevation, buccal-lingual side elevation, and bottom views, respectively, of a shell for a molar according to the fourth embodiment of the invention.
Figure 30:
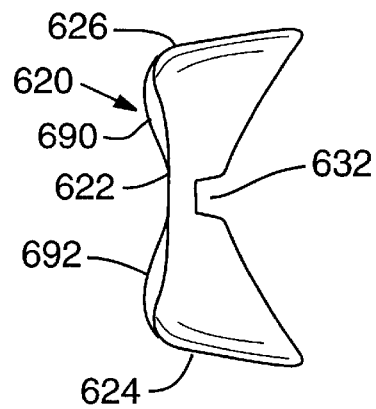
Figure 31:
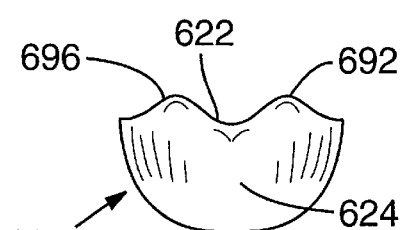
Figure 32:
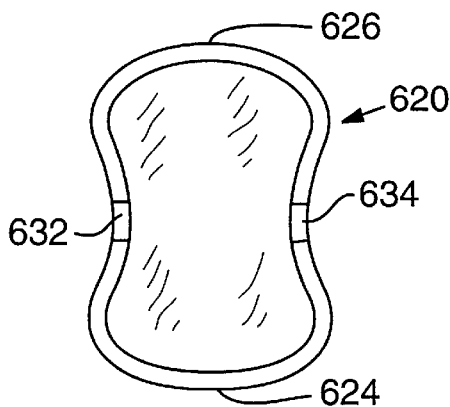

The occlusal wall is preformed to approximate the anatomy of a natural human tooth. Referring specifically to FIG. 29, the molar shell 620 of the fourth embodiment has four protuberances 690, 692, 694, 696 on its occlusal surface 622, which are flattened on top, to approximate a biting surface of a tooth. The four protuberances are oriented in opposing pairs in a buccal-lingual direction, and are arranged to position one protuberance in each quadrant of the occlusal surface. Referring to FIG. 25, the shell 520 designed for a bicuspid tooth has only two protuberances, which are similar to those of the molar shell 620.

As with the other embodiments, the fourth embodiment incorporates a design that only requires a few shells to fit the dentition of a wide range of adults. A kit based on this embodiment can contain a set of either of two types of crowns—temporary and long-term provisional crowns. Eight sizes and shapes of temporaries are provided. Sixteen sizes and shapes of long-term provisionals are provided. Long-term provisionals have more sizes of shells to provide a more accurate fit, and are made of a more durable polycarbonate material. Temporary shells can be made with thinner walls, as they do not have to last as long.

An adult kit having shells for temporary bicuspid and molar crowns of adult teeth according to the fourth embodiment, for example, consists of eight sizes and shapes of shells. Two sizes of shells are used for molars in the upper right portion of the jaw and two other sizes of shells are used for molars in the upper left portion of the jaw. Another two shells are used for molars in the lower jaw (interchangeably on either the right or left sides), and the final two shells are used interchangeably for bicuspids in either the upper or lower jaw, interchangeably on either the right or left side.

Accordingly, a set of temporary shells in an adult kit includes two upper right molar shells, two upper left molar shells, two lower molar shells, and two bicuspid shells. A top view of each of the two upper right molar shells has an approximate parallelogram shape leaning to the right while a top view of each of the two upper left molar shells has an approximate parallelogram shape leaning to the left. The two lower molar shells have a top view with an approximate rectangular shape. And finally, a top view of the two bicuspid shells has an approximate oval shape. Adult kits for long-term provisional crowns contain sixteen sizes and shapes of shells to provide even better sizing options. Similar kits can be made for children.

FIGS. 33–35 show sizing considerations for a molar shell 620 and FIGS. 36–44 show a method for making a crown using the molar shell 620. The same technique is used for making crowns using both temporary and long-term provisional shells. FIG. 33 shows a prepared tooth 660 and the adjacent inter-dental papilla 72.

Figure 36:
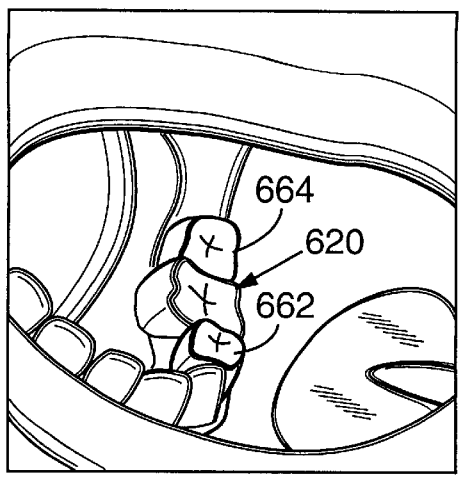
FIGS. 36–44 illustrate the steps of a method for preparing a temporary or permanent crown according to the invention, using the shell of FIGS. 33–35.

A preferred method for installing the temporary or long-term provisional crowns of this invention proceeds as follows. First, the tooth 660 to be crowned is prepared. Referring now to FIGS. 34, 35, and 36, a shell of the proper mesio-distal and occluso-gingival sizes must then be selected. A properly sized shell 660 fits passively and comfortably within the space provided in the patient's dentition between adjacent teeth 662, 664 and opposite teeth (not shown), i.e., fitting both the margins and occlusions well. For instance, the shell can be sized so that the occlusal surface profile has a mesio-distal width adjacent each of the buccal and lingual sidewalls that approximates a medial mesio-distal spacing of teeth adjacent the prepared tooth. The concave mesio-distal sidewalls 632, 634 further conform to the convex sidewalls of adjacent teeth 662, 664 to form a substantially uniform proximal gap 80 for receiving extruded resin 638A and 636A. A suitable proximal gap is typically less than 1 mm in width, with a width of about 0.5 mm being preferred.

Figure 37:
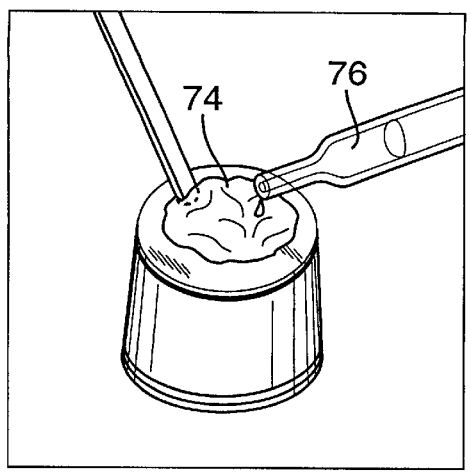
Figure 38:
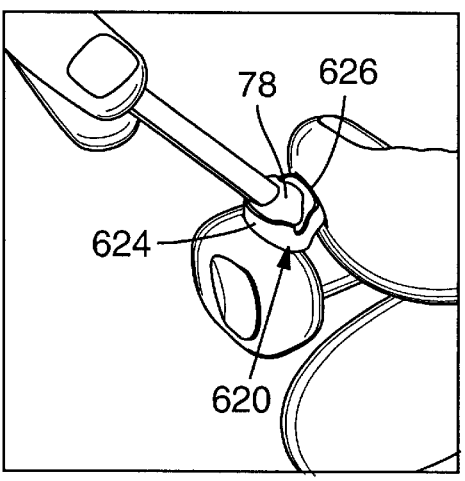

Next, as illustrated in FIG. 37, resin is prepared by slowly mixing Super-T acrylic resin powder 74 with a reactive liquid 76 until the liquid completely saturates the powder and the combination becomes a creamy consistency. This mixture is then allowed to set for approximately 20 seconds. As shown in FIG. 38, the shell 620 then is filled with a quantity of the resin 78 up to the height of the buccal and lingual sidewalls 624, 626.

Figure 39:
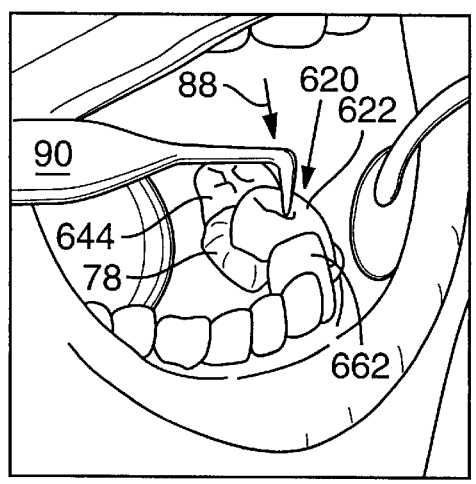

The resin-filled shell 620 is then positioned on the prepared tooth 660 as shown in FIG. 39. A hand instrument 90 (i.e., Grade 4–5) is used to apply vertical pressure (represented by arrow 88) to the center of the shell 620 to properly position the shell over the prepared tooth and between adjacent teeth 662, 664. The patient then bites down lightly to extrude resin from the windows in the mesio-distal sidewalls and out from the gingival margins and to align the occlusal surface 622 of the shell 620 with the occlusal surfaces of adjacent teeth 662, 664. The dentist or technician could, alternatively, visually align the occlusal surface 622 of the shell 620 with the occlusal surfaces of the adjacent teeth 662, 664. The shell 620 and resin are left in place on the prepared tooth for approximately 10 seconds to allow the resin to partially set. After the resin becomes a little bit tacky, the hand instrument can then be used to remove some of the excess resin 78. Removing excess resin at this stage cuts down on the trimming time required later.

Once the resin is putty-like, the resin-filled shell is repeatedly removed from and placed back on the prepared tooth until the resin has completely set. It is important during this step not to lift the crown too far off the prepared tooth (for example, do not lift more than a centimeter from the prepared tooth) and not to leave it off the prepared tooth for too long. This step further causes the resin to extrude through the windows of the mesio-distal sidewalls while preventing the shell 620 from locking onto the prepared tooth. After a few repetitions, the patient should then bite down again lightly. The shell 620 should then be lifted off and replaced yet again to prevent any undercuts. Even after the resin becomes stiff, some shrinkage will still occur. Therefore, the shell 620 should not be completely removed from the prepared tooth until the resin is completely set (about an extra minute or two). It should be noted that the reaction which causes the resin to set is slightly exothermic, but does not produce a significant amount of heat in this case because only a small amount of material is used.

Figure 40:
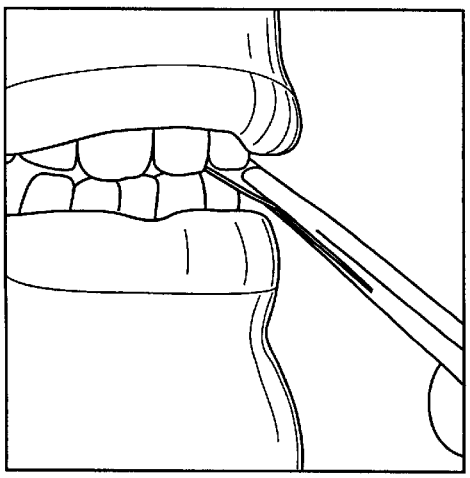

While waiting for the resin to finish setting, the occlusions can be adjusted, as represented in FIG. 40. Carbon paper can be used to mark occlusions on the crown for adjustment. To mark the occlusions, carbon paper is placed between opposing teeth. The patient then bites down and grinds the opposing teeth together. The occlusions marked by the carbon can then be adjusted using a diamond bit. This process is repeated until carbon appears on adjacent teeth, indicating that contact is being made between opposing and adjacent teeth, and therefore that a good occlusion has been obtained.

Figure 41:
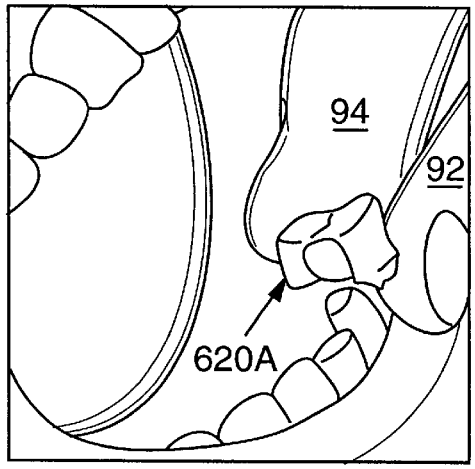
Figure 42:
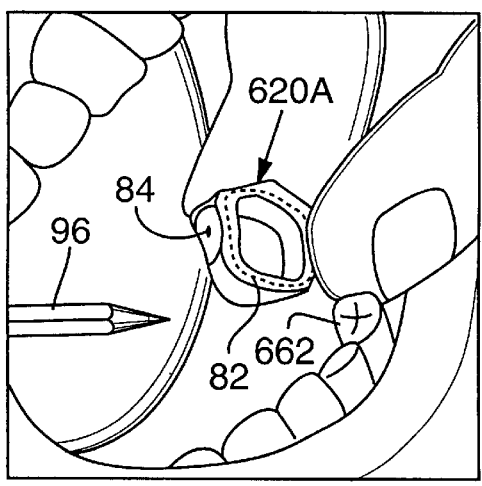

Once the resin is completely set, the crown 620A can be removed from the prepared tooth 660, as shown in FIG. 41. The crown 620A is removed from the prepared tooth 660 by lifting it vertically using either a finger 92 and thumb 94 or a crown remover (not shown). Margins 82 and contacts with adjacent teeth 84 are then marked with a pencil 96, as shown in FIG. 42, to enhance their visibility during the trimming operation. The adjacent contacts 84 should be kept wide for a good crown fit between the adjacent teeth. Once the margins and contacts are marked, the crown can be trimmed and finished, as illustrated in FIG. 43.

Figure 43:
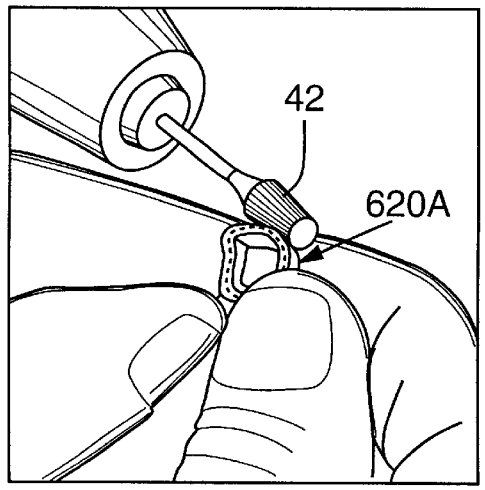

Referring now to FIG. 43, it is important to perform the steps of the trimming process in the following order. The four corners are trimmed first to the marked margins using an acrylic bur lathe 42 or chair-side acrylic bur (not shown). The buccal, lingual, and mesio-distal walls are trimmed next to the marked margins. The acrylic bur is then used to trim underneath the marked contacts. The crown 620A is then finished and polished using a rubber wheel.

Figure 44:
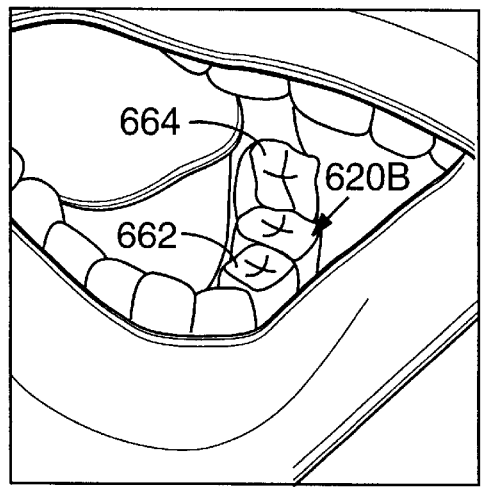

Referring to FIG. 44, in the case of a long-term provisional crown 620B, the crown 620B should be relined if necessary. Using a medium-size round bur, the dentist or technician should grind inside of the shell right at the margins. More resin can be added if needed. The sulcus can also be packed with a retraction cord for better fit.

Referring again to FIG. 35, when the crown 620C is finished, it is ready to be secured within the patient's mouth. The crown 620C is seated on the prepared tooth 660 and checked for fit. The dentist should make sure both the contours and margins are good. A final bite adjustment is therefore done to verify that the crown has tight-fitting adjacent contacts, good margins, and good occlusion.

One of the major advantages of crowns made using the shells of FIGS. 25–32 is that the occlusal anatomy is already built into the shells. This saves a significant amount of time which would otherwise be required to trim and form the occlusal surface. To ensure a good fit, some of the anatomy can still be taken away with occlusion adjustment to remove lateral and protrusive interferences. When the fit looks good, the crown 620C is then cemented onto prepared tooth 660 along the gingival margins.

Having described and illustrated the principles of the invention in several preferred embodiments thereof, it should be apparent that the invention can be modified in arrangement and detail without departing from such principles. Various novel features described herein can be used in different combinations and can be modified in shape and dimension without exceeding the scope of the invention. I therefore claim all modifications and variations coming within the spirit and scope of the following claims.

I claim:

1. A shell for making a temporary or long-term provisional crown a prepared tooth, comprising:

a top wall defining an occlusal surface;

a buccal sidewall;

a lingual sidewall spaced apart from the buccal sidewall;

opposite mesio-distal sidewalls, each connected to the top wall and to the buccal and lingual sidewalls, and being spaced apart from each other to define a central cavity configured to receive resin and to fit passively over a prepared tooth;

each of the sidewalls having a gingival margin;

each of the mesio-distal sidewalls having a window forming a partial opening in the sidewall for allowing a portion of the resin to protrude from the cavity mesio-distally to an adjacent tooth; and the windows being positioned along the gingival margin of the mesio-distal sidewalls intermediate the buccal and lingual sidewalls and having a generally U-shape opening to the gingival margin and a size less than one-fourth of the area of the mesio-distal sidewall;

each of the mesio-distal sidewalls shaped to interfit conformally with a convex mesio-distal surface of the adjacent tooth to provide a proximal gap shaped to control resin flow from the windows between the shell and each of the adjacent teeth.

2. A shell according to claim 1, wherein the mesio-distal sidewalls are shaped so that the proximal gap has an approximately uniform-width.

3. A shell according to claim 1, wherein the top wall defining the occlusal surface has an approximately hourglass shape.

4. A shell according to claim 3, wherein the hourglass shape of the occlusal surface conforms with mesio-distal surfaces of adjacent teeth in way that controls a proximal flow of the resin.

5. A shell according to claim 1, wherein the buccal and lingual sidewalls are sized to contact an inter-dental papilla between the prepared tooth and the adjacent teeth.

6. A shell according to claim 1, wherein the shell is designed for a molar tooth and the occlusal sidewall has four protuberances to approximate a biting surface of a natural human tooth.

7. A shell according to claim 6, wherein the four protuberances are oriented in pairs aligned in a buccal-lingual direction, and are arranged to position one protuberance in each quadrant of the occlusal sidewall.

8. A shell according to claim 1, wherein the shell is designed for a bicuspid tooth and the occlusal surface has two protuberances arranged to approximate a biting surface of a natural human tooth.

9. A shell according to claim 8, wherein the two protuberances are oriented in an opposing pair aligned in a buccal-lingual direction.

10. A set of shells according to claim 1, including two upper right molar shells, two upper left molar shells, two lower molar shells, and two bicuspid shells.

11. A set of shells according to claim 10, wherein a top view of each of the two upper right molar shells has an approximate parallelogram shape leaning to the right.

12. A set of shells according to claim 10, wherein a top view of each of the two upper left molar shells has an approximate parallelogram shape leaning to the left.

13. A set of shells according to claim 10, wherein a top view of each of the two lower molar shells has an approximate rectangular shape.

14. A set of shells according to claim 10, wherein a top view of each of the two bicuspid shells has an approximate oval shape.

15. A method of fabricating temporary or long-term provisional crowns for molars and bicuspids for placement in a patient's mouth, the method comprising:

filling a central cavity of a shell comprising a top wall defining an occlusal surface, opposite buccal and lingual sidewalls, and opposite mesio-distal sidewalls spaced apart to define the central cavity, with a quantity of resin;

forming the shell so that the top wall has a profile in plan view that is concave along its mesio-distal sides;

positioning the resin-filled shell on a prepared tooth proximal to a convex mesio-distal side of an adjacent tooth;

extruding a portion of the resin mesio-distally through a window forming a partial opening in at least one of the mesio-distal sidewalls into a recessed area adjoining the window along the mesio-distal sidewall, the concavity of the recessed area and convexity of the adjacent tooth controlling and directing the extruded resin;

pulling the resin-filled shell off the prepared tooth when the resin is set; and shaping the shell and extruded resin to contour an external surface thereof to fit occlusally and proximally into the patient's mouth.

16. A method according to claim 15, wherein the mesio-distal sidewalls are formed in alignment with the concave profile of the top wall.

17. A method according to claim 15, wherein the shell is sized so that the top wall profile has a mesio-distal width adjacent each of the buccal and lingual sidewalls that approximates a medial mesio-distal spacing of teeth adjacent to the prepared tooth.

18. A method according to claim 15, wherein the shell is sized and shaped to form a substantially uniform-width proximal gap between the mesio-distal sidewalls and the adjacent teeth when positioned in the patient's mouth.

19. A method according to claim 15, wherein the shell is sized and shaped to provide the top wall with an approximate hourglass shape profile conforming to convex mesio-distal sides of adjacent teeth, and wherein a mesio-distal gap having a substantially uniform-width is provided to control the mesio-distal extrusion of the resin.

20. A method according to claim 15, further comprising:
    marking the mesio-distal contacts and margins;
    removing resin that has extruded through the window in the mesio-distal sidewall beyond the marked contacts and margins; and
    repositioning the resin-filled shell on the prepared tooth.

21. A method according to claim 20, wherein the steps of marking and removing are performed with the resin-filled shell removed from the prepared tooth.

22. A method according to claim 15, including repeatedly pulling the resin-filled shell off and putting the resin-filled shell on the prepared tooth until the resin is set, without closing the patient's mouth.

23. A method according to claim 15, wherein the resin includes a quantity of Ti particles to enhance crown durability.

24. A shell for making a temporary or long-term provisional crown on a prepared tooth, comprising:
    a top wall comprising an occlusal surface, a lingual side, a buccal side, and two mesio-distal sides, said top wall having a concave indentation along each of the mesio-distal sides thereof;
    a buccal sidewall connected to the top wall;
    a lingual sidewall connected to the top wall and spaced apart from the buccal sidewall; and
    opposite mesio-distal sidewalls each connected to the top wall and to the buccal and lingual sidewalls, the mesio-distal sidewalls being spaced apart from each other to define a central cavity configured to receive resin and to fit over a prepared tooth, each of the mesio-distal sidewalls having a window forming a partial opening in the sidewall for allowing a portion of the resin to protrude from the cavity mesio-distally to a corresponding adjacent tooth, and each of the mesio-distal sidewalls shaped concavely to interfit conformally with a convex mesio-distal surface of the corresponding adjacent tooth.

25. A shell according to claim 24, wherein
    the top wall is shaped concavely along edges connected to each of the mesio-distal sidewalls so as to conform proximally to a convex shape of mesio-distal surfaces of adjacent teeth.

26. A shell according to claim 25, wherein both of the mesio-distal sidewalls are shaped concavely to align with the concave shape of the top wall.

27. A shell according to claim 25, wherein the buccal and lingual sidewalls each have an approximately triangular shape.

28. A shell according to claim 25, wherein the lingual sidewall has a length that is not greater than a length of the buccal sidewall.

29. A shell according to claim 28, in which the mesio-distal sidewalls have a length less than the length of the lingual sidewall.

30. A shell according to claim 24 in which
    at least one of the mesio-distal sidewalls has a generally U-shaped window which is unbounded along a gingival periphery of the mesio-distal sidewalls, the window having a size sufficient for resin to protrude from the cavity mesio-distally in an amount sufficient to form a proximal contact to the adjacent tooth but sufficiently smaller than a surface area of the mesio-distal sidewall of the shell to control a flow of the resin from the cavity.

31. A shell according to claim 30 in which the size of the window is not greater than about $\frac{1}{4}^{th}$ the surface area of the mesio-distal sidewall.

32. A shell according to claim 30 in which the size of the window is approximately $\frac{1}{8}$ to $\frac{1}{10}$ the surface area of the mesio-distal sidewall.

33. A shell according to claim 30 in which the top wall is indented along mesio-distal sides thereof and wherein the mesio-distal sidewalls are shaped to conform to the indentation of the top wall.

34. A shell according to claim 30 wherein at least one of the mesio-distal sidewalls is shaped to interfit conformally with a convex mesio-distal surface of the adjacent tooth.

35. A shell according to claim 34, wherein the mesio-distal sidewall shaped to interfit conformally interfits with the adjacent tooth to provide a proximal gap shaped to control resin flow between the shell and the adjacent tooth.

* * * * *

UNITED STATES PATENT AND TRADEMARK OFFICE
CERTIFICATE OF CORRECTION

PATENT NO. : 6,257,892 B1
DATED : July 10, 2001
INVENTOR(S) : Worthington

It is certified that error appears in the above-identified patent and that said Letters Patent is hereby corrected as shown below:

Title page,
Item [60], Related U.S. Application Data, should include -- Provisional application No. 60/131,817, filed on April 29, 1999. --.

Column 3,
Line 43, "the patient' mouth." should read -- the patient's mouth. --.

Column 13,
Line 48, "crown a prepared tooth," should read -- crown on a prepared tooth, --.

Column 14,
Line 14, "teeth in way" should read -- teeth in a way --.

Signed and Sealed this

Third Day of May, 2005

JON W. DUDAS
*Director of the United States Patent and Trademark Office*